(12) United States Patent
Arima

(10) Patent No.: US 9,131,593 B2
(45) Date of Patent: Sep. 8, 2015

(54) RADIATION IMAGING CONTROL APPARATUS, RADIATION IMAGING SYSTEM, AND STORAGE MEDIUM

(71) Applicant: CANON KABUSHIKI KAISHA, Tokyo (JP)

(72) Inventor: Keisuke Arima, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 112 days.

(21) Appl. No.: 13/915,878

(22) Filed: Jun. 12, 2013

(65) Prior Publication Data

US 2013/0336458 A1    Dec. 19, 2013

(30) Foreign Application Priority Data

Jun. 15, 2012   (JP) .................. 2012-135832

(51) Int. Cl.
- *H05G 1/60* (2006.01)
- *H05G 1/30* (2006.01)
- *G06F 19/00* (2011.01)
- *A61B 6/00* (2006.01)

(52) U.S. Cl.
CPC ........ *H05G 1/30* (2013.01); *A61B 6/548* (2013.01); *A61B 6/563* (2013.01); *G06F 19/321* (2013.01); *A61B 6/542* (2013.01)

(58) Field of Classification Search
CPC .............. H05G 1/60; H05G 1/30; H05G 1/58; A61B 6/46; A61B 6/463; A61B 6/465; A61B 6/469; G06F 19/3406; G06F 19/3412
USPC .................................. 378/98, 98.2, 114, 115
See application file for complete search history.

(56) References Cited

U.S. PATENT DOCUMENTS

| | | |
|---|---|---|
| 2011/0051896 A1 | 3/2011 | Abe |
| 2011/0170669 A1 | 7/2011 | Nakatsugawa et al. |

FOREIGN PATENT DOCUMENTS

| | | |
|---|---|---|
| CN | 102379708 A | 3/2012 |
| EP | 2244202 A2 | 10/2010 |
| JP | 2003245270 A | 9/2003 |
| JP | 2005196535 A | 7/2005 |
| JP | 4337133 B2 | 9/2009 |
| JP | 2010253044 A | 11/2010 |
| JP | 4764098 B2 | 8/2011 |
| JP | 2012024204 A | 2/2012 |
| JP | 2012146044 A | 8/2012 |

*Primary Examiner* — Jurie Yun

(74) *Attorney, Agent, or Firm* — Canon USA Inc. IP Division

(57) ABSTRACT

A radiation imaging control apparatus includes a reception unit configured to receive at least one piece of order information for radiation imaging, a transmission unit configured to transmit, to an external device, a first signal indicating that radiation imaging for the order information is started in response to an instruction being issued for starting radiation imaging corresponding to at least one of pieces of the received order information and to transmit, to an external device, a second signal indicating that radiation imaging for the order information is finished in response to radiation imaging corresponding to the order information being finished, and a control unit configured to limit a transmission of the first signal by the transmission unit if an instruction for starting radiation imaging for the finished order information is issued again.

23 Claims, 16 Drawing Sheets

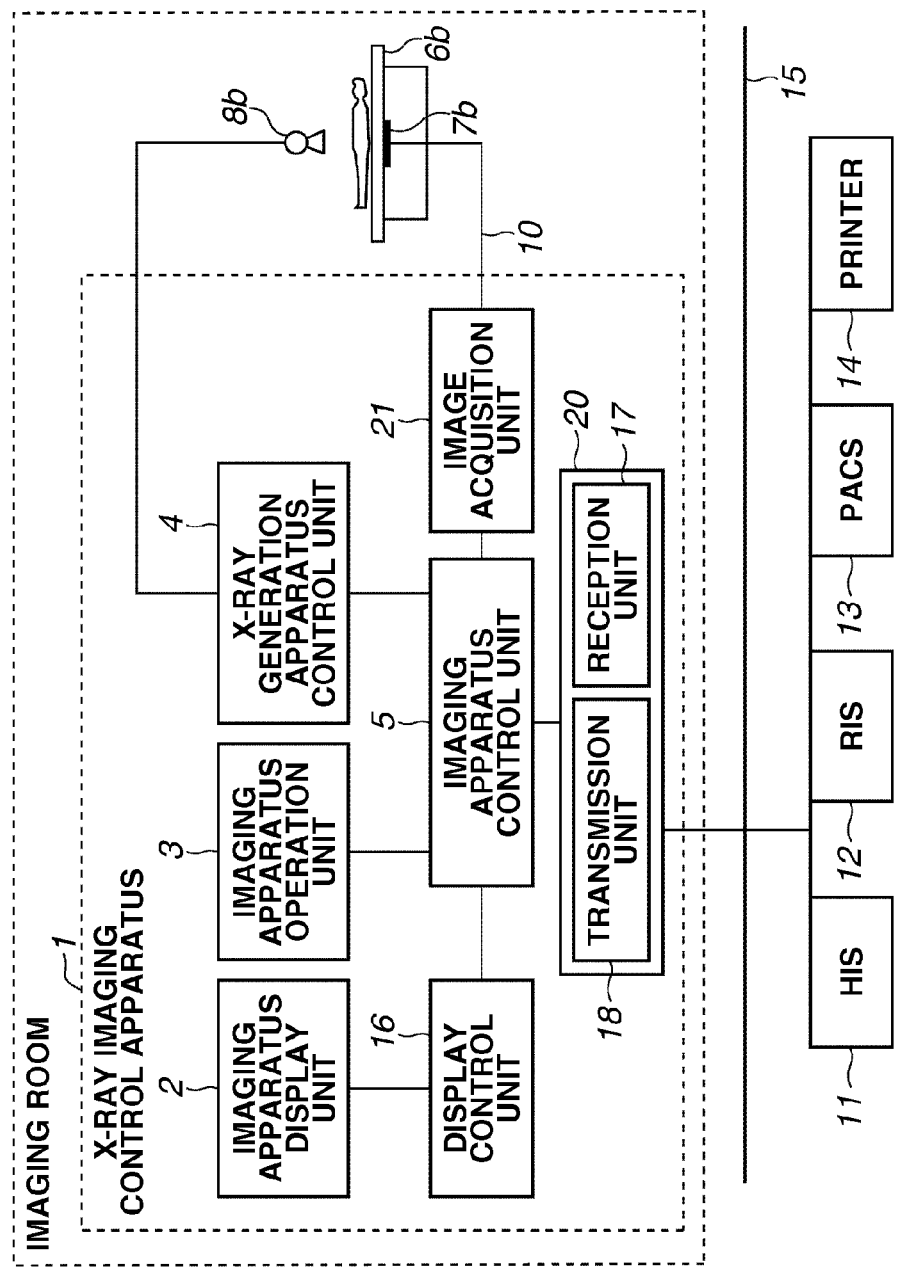

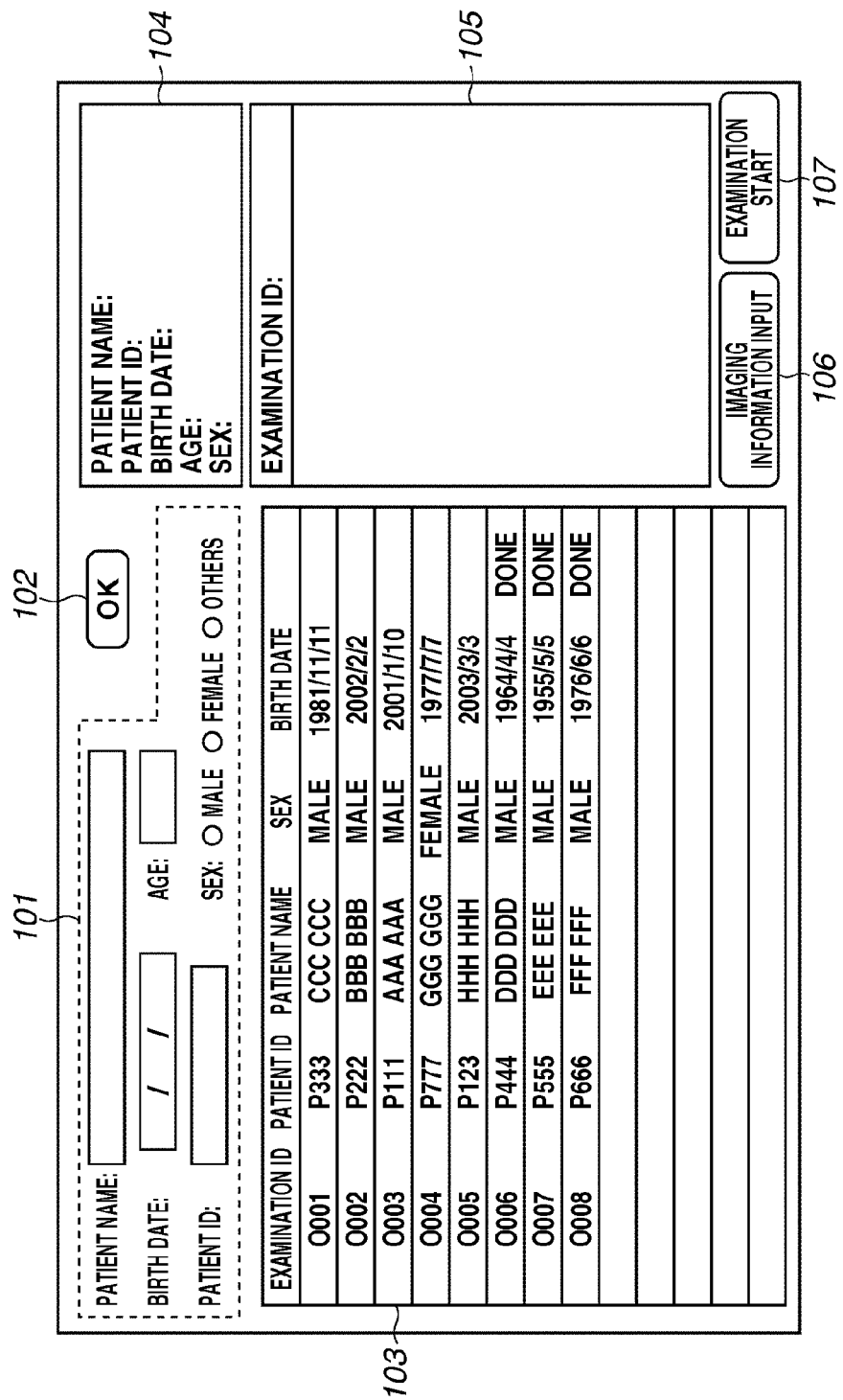

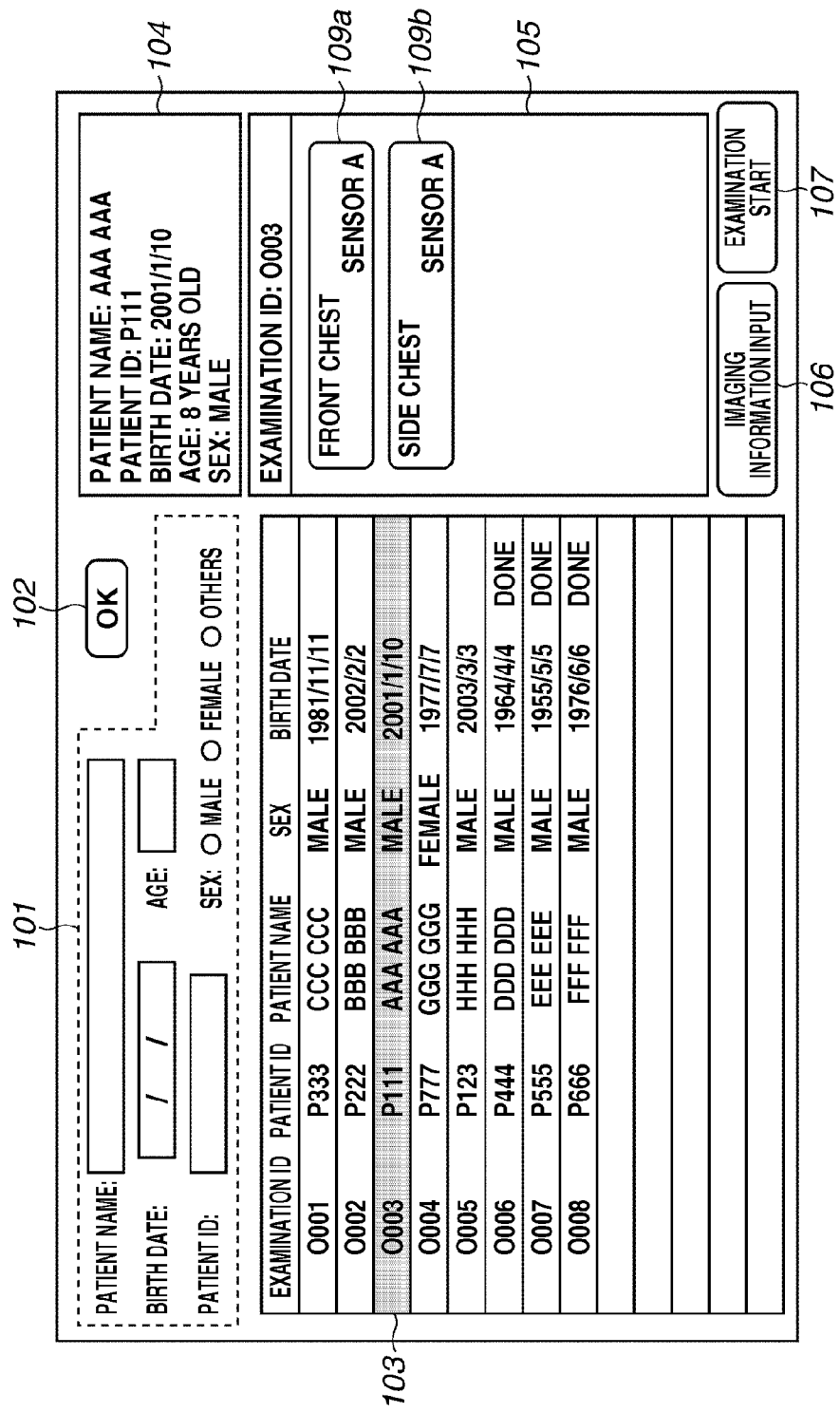

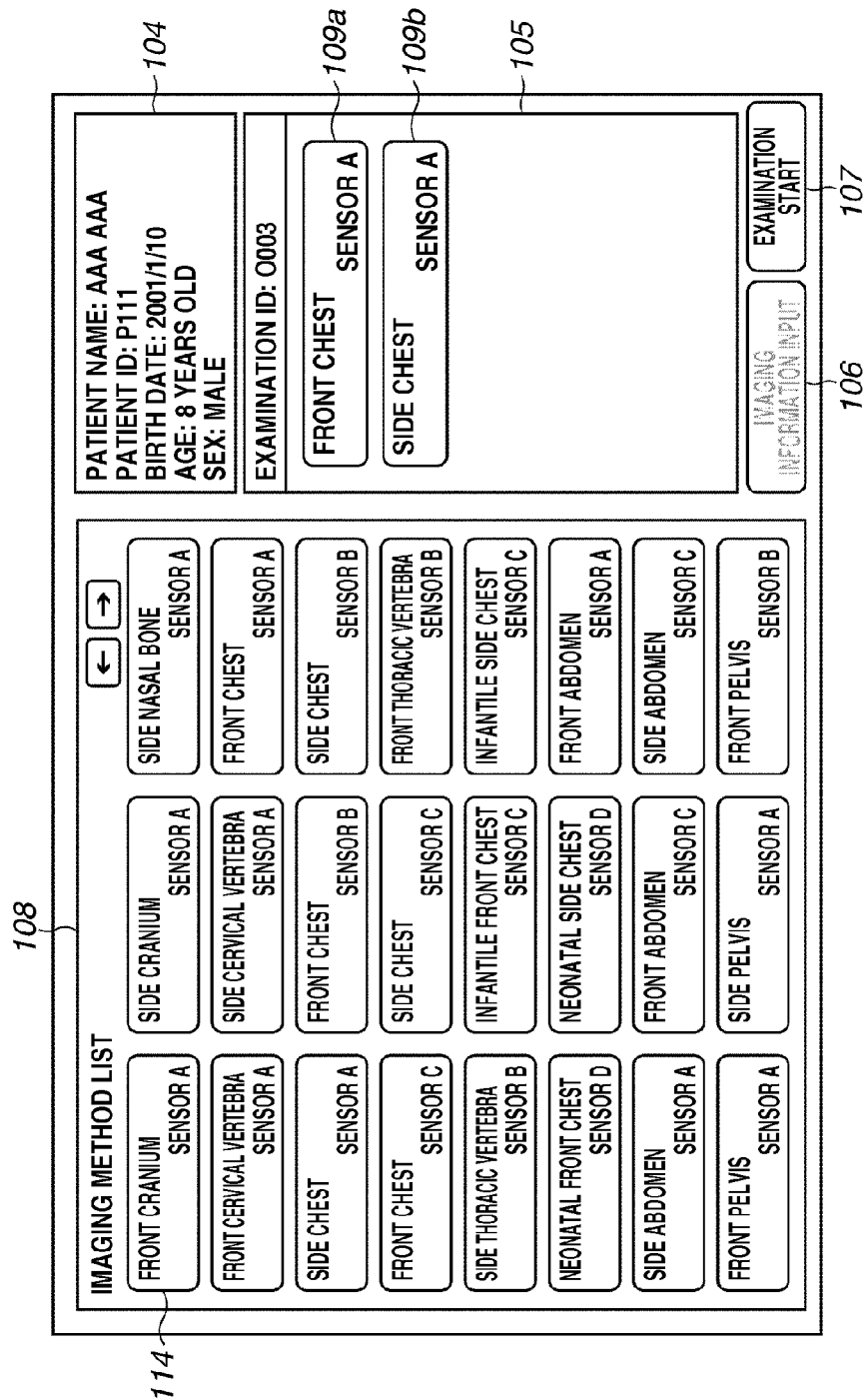

PAST EXAMINATION LIST

| EXAMINATION ID | PATIENT ID | PATIENT NAME | SEX | BIRTH DATE |
|---|---|---|---|---|
| O001 | P333 | CCC CCC | MALE | 1981/11/11 |
| O002 | P222 | BBB BBB | MALE | 2002/2/2 |
| O003 | P111 | AAA AAA | MALE | 2001/1/10 |
| O004 | P777 | GGG GGG | FEMALE | 1977/7/7 |
| O005 | P123 | HHH HHH | MALE | 2003/3/3 |
| O006 | P444 | DDD DDD | MALE | 1964/4/4 |
| O007 | P555 | EEE EEE | MALE | 1955/5/5 |
| O008 | P666 | FFF FFF | MALE | 1976/6/6 |

302

EXAMINATION RESUMPTION

| EXAMINATION ID | EXAMINATION DATE | PATIENT ID | PATIENT NAME | BIRTH DATE | SEX | NUMBER OF CAPTURED IMAGES | NUMBER OF FILMS |
|---|---|---|---|---|---|---|---|
| O006 | 2012/6/1 12:00 | P444 | DDD DDD | 1964/4/4 | MALE | 2 | 0 |
| O007 | 2012/6/2 9:00 | P555 | EEE EEE | 1955/5/5 | MALE | 3 | 2 |
| O008 | 2012/6/1 18:00 | P666 | FFF FFF | 1976/6/6 | MALE | 4 | 4 |
| | | | | | | | |
| | | | | | | | |
| | | | | | | | |

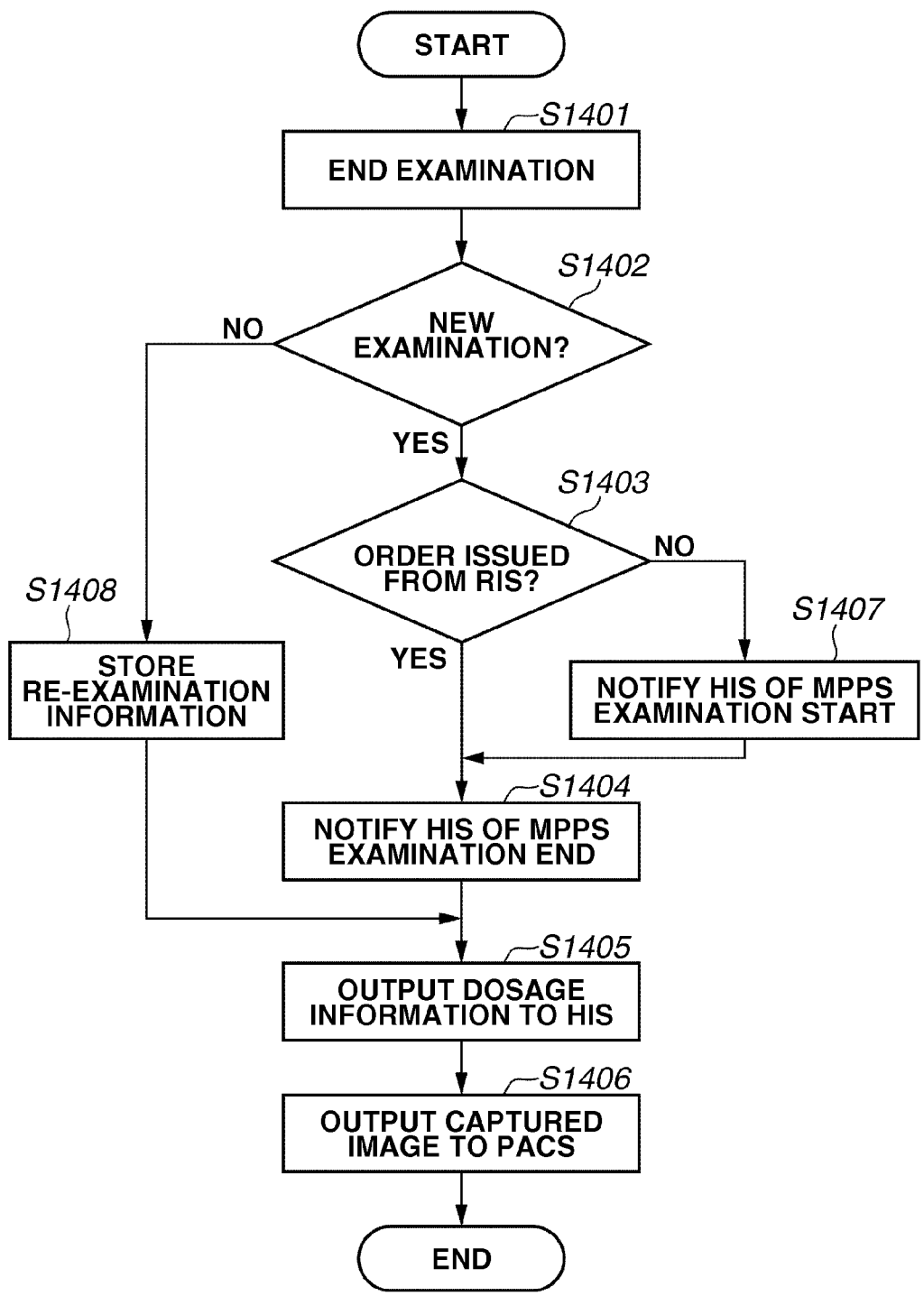

US 9,131,593 B2

RADIATION IMAGING CONTROL APPARATUS, RADIATION IMAGING SYSTEM, AND STORAGE MEDIUM

BACKGROUND OF THE INVENTION

1. Field of the Invention

The present invention relates to a radiation imaging control apparatus, a radiation imaging system, and a storage medium.

2. Description of the Related Art

In recent years, a hospital information system which is connected via a network has been constructed in a hospital. For example, if X-ray imaging is determined to be required, examination instructions are input from a terminal of a hospital information system (HIS) to be transferred to a radiation department, which is a request receiving side. The requested information is called an examination order, which includes a department name of a request sending side, examination items, and personal data of a patient. When the radiation department receives the examination order via a radiology information system (RIS), the radiation department adds imaging conditions to the examination order and transfers the examination order to an X-ray examination system. The X-ray examination system performs X-ray imaging according to the received examination order. The captured image is added to examination information, transferred to a picture archiving and communication system (PACS), and printed. Implementation information about the examination by the X-ray examination system is transferred to the HIS. The implementation information transferred to the HIS is used for account processing after the examination as well as for the progress management of the examination.

Recently, there has been an Integrating the Healthcare Enterprise (IHE) technical framework, which is a guideline for the purpose of promoting the multi-vendor in a hospital system and is adapted for various use cases in a clinical site.

In the clinical site, in addition to the examination order placed via the RIS, there are often requested re-imaging due to failure in imaging and re-examination such as additional imaging based on the results of a medical doctor's diagnosis. In the above IHE technical framework, it is not allowed to start re-examination or add imaging afterward with respect to the examination in which the HIS is notified that the examination has been finished. Instead, it is recommended that the RIS issues a new examination.

In the re-examination performed immediately after the examination is finished, a patient may be overloaded depending on the lead time required for the issuance of a new examination. For the case of examination using a portable X-ray examination system, an examination place is not necessarily suited to an environment where the system can be connected to a network, so that it is possible that a re-examination order cannot be placed.

SUMMARY OF THE INVENTION

According to an aspect of the present invention, a radiation imaging control apparatus includes a reception unit configured to receive at least one piece of order information for radiation imaging, a transmission unit configured to transmit, to an external device, a first signal indicating that radiation imaging for the order information is started in response to an instruction being issued for starting radiation imaging corresponding to at least one of pieces of the received order information and to transmit, to the external device, a second signal indicating that radiation imaging for the order information is finished in response to radiation imaging corresponding to the order information being finished, and a control unit configured to limit a transmission of the first signal by the transmission unit if an instruction for starting radiation imaging for the finished order information is issued again.

Further features of the present invention will become apparent from the following description of exemplary embodiments with reference to the attached drawings.

BRIEF DESCRIPTION OF THE DRAWINGS

FIG. 1 is a block diagram illustrating a configuration of a medical examination system according to a first exemplary embodiment of the present invention.

FIGS. 2A, 2B, and 2C illustrate examples of new examination input screens.

FIG. 3A illustrates a past examination list indicating the finished examination. FIG. 3B illustrates an example of a re-examination information table.

FIG. 14 is a flow chart illustrating a flow of processing at the time of finishing examination according to the fifth exemplary embodiment.

DESCRIPTION OF THE EMBODIMENTS

Figure 4:
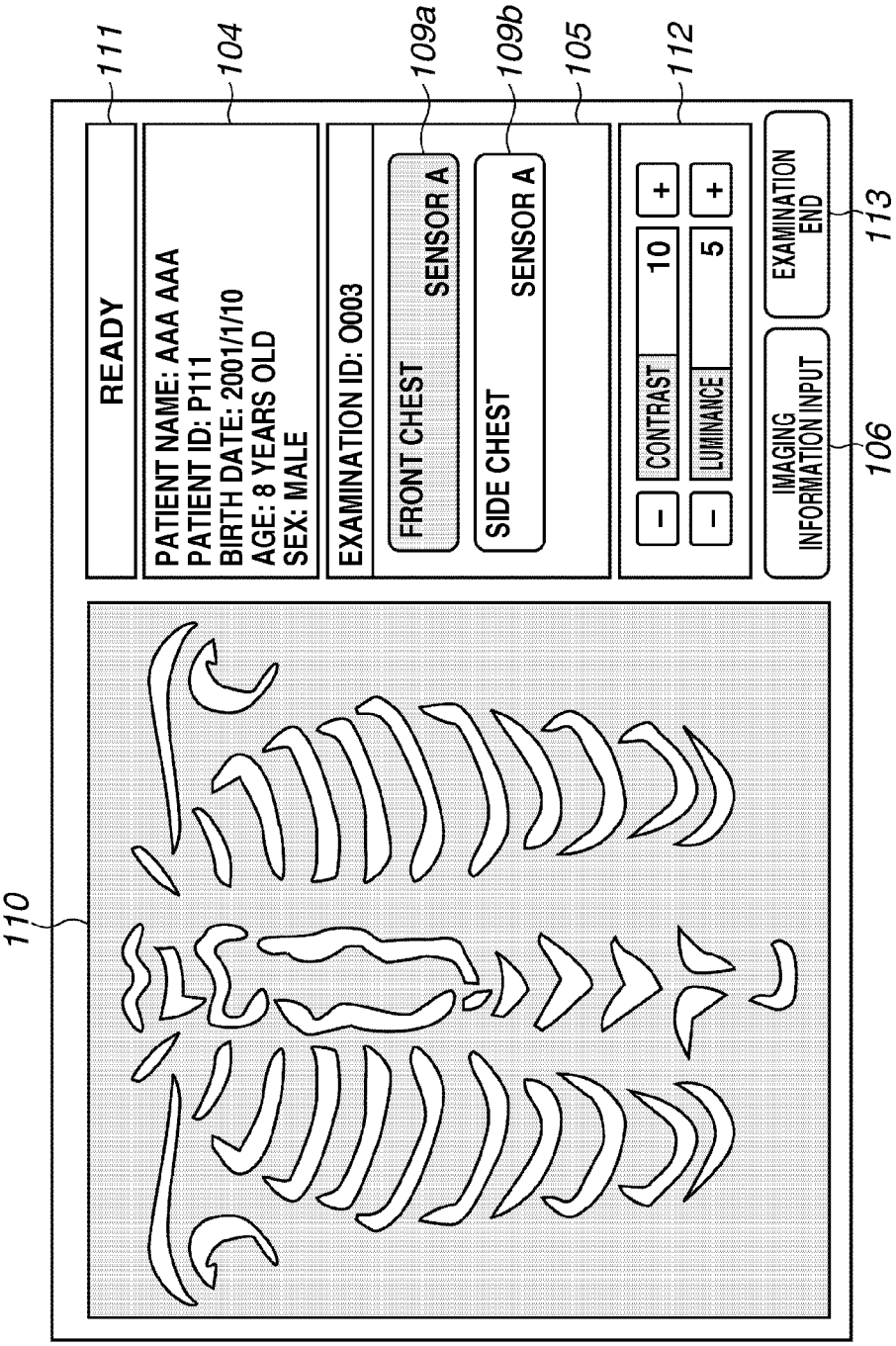
FIG. 4 is an example of an imaging screen.

FIG. 1 is a block diagram illustrating an example of configuration of a radiation imaging system (hereinafter referred to as an X-ray imaging system) according to a first exemplary embodiment of the present invention.

In the X-ray imaging system, an X-ray imaging control apparatus 1, a departmental radiology information system (RIS) 12, a PACS (an image server) 13, and a hospital information system HIS 11 for managing the progress of radiation imaging are connected to one another. The HIS 11 can include a server which manages account information. If it is determined that X-ray imaging is required, examination instructions are input from a terminal of the hospital information system (HIS) and transferred to a radiation department, which is a request receiving side. The requested information is called an examination order, which includes a department name of a request sending side, examination items, and personal data of a patient. When the radiation department receives the examination order via the radiology information system (RIS), the radiation department adds imaging conditions to the examination order and transfers the examination order to an X-ray examination system. The X-ray examination system performs X-ray imaging according to the received examination order. The captured image is added to examination information, transferred to the picture archiving and communication systems (PACS), and printed. Information about the execution of examination by the X-ray examination system is transferred to the HIS. The implementation information transferred to the HIS is used for account processing after the examination as well as for the progress management of the examination.

The above apparatuses are connected to one another via a network 15 such as a local area network (LAN) or a wide area network (WAN), for example. Each of the apparatuses includes one or a plurality of computers. The computer is provided with a main control unit such as a central processing unit (CPU) and a storage unit such as a read only memory (ROM) and a random access memory (RAM), for example. The computer may be provided with a communication unit such as a network card and an input output unit such as a keyboard, a display, or a touch panel. These component units are connected to one another via a bus and controlled by the main control unit executing the programs stored in the storage units.

The X-ray imaging control apparatus 1 includes an imaging apparatus display unit 2, an imaging apparatus operation unit 3, an X-ray generation apparatus control unit 4, an imaging apparatus control unit 5, a display control unit 16, a communication unit with a reception unit 17 and a transmission unit 18, and an image acquisition unit 21.

The X-ray generation apparatus control unit 4 is connected to an X-ray generation unit 8 via a cable 9 to control the irradiation of X rays from the X-ray generation unit 8. The X-ray generation unit 8 (8a and 8b) functions as a radiation generation unit. The X-ray generation unit 8 is realized by an X-ray tube, for example, and irradiates an object (a specific region of a patient, for example) with X-rays.

The imaging apparatus operation unit 3 comprehensively controls processing in the X-ray imaging control apparatus 1. The imaging apparatus display unit 2 is realized by a liquid crystal display, for example, and displays various pieces of information for an operator (a radiologist or a medical doctor). The imaging apparatus operation unit 3 is realized by a mouse and an operation button, for example, and inputs various instructions from the operator to the apparatus. The imaging apparatus display unit 2 and the imaging apparatus operation unit 3 may be realized by a touch panel integrally formed of these units.

The X-ray imaging control apparatus 1 is connected to an X-ray detector 7 (7a and 7b) via a cable 10 and transfers/receives power supply and image and control signals to/from the X-ray detector 7 via the cable 10. The X-ray detector 7 detects the X rays passing through the object and functions as a detector which acquires an X-ray image (a radiation image) based on the object. In other words, the X-ray generation unit 8 and the X-ray detector 7 are collaboratively operated to realize an X-ray imaging unit. The X-ray detector 7 is installed on an upright or a lying imaging table 6 (6a and 6b).

In the radiation imaging system, the reception unit 17 in the communication unit 20 receives one or a plurality of pieces of order information about radiation imaging from the RIS 12. The order information includes information about a subject and one or a plurality of imaging target regions of the subject, for example.

The imaging apparatus control unit 5 functions as an instruction unit configured to issue instructions for starting radiation imaging corresponding to at least one of pieces of the received order information. The instructions for starting radiation imaging are issued by the imaging apparatus operation unit 3 receiving the input from the user, for example. Alternatively, the instructions may be issued by the imaging apparatus control unit 5 selecting the order information to be imaged.

The transmission unit 18 transmits, to the HIS 11, information (a first signal) indicating that the radiation imaging about the order information is started in response to the instructions for starting radiation imaging. Thus, the HIS 11 changes the status about the order to the status indicating that the examination is started. Thereafter, when all radiation imaging operations corresponding to the order information are finished and the user performs input for confirming the completion of the order via the imaging apparatus operation unit 3, the transmission unit 18 transmits, to the HIS 11, information (a second signal) indicating that the radiation imaging about the order information is finished. Thus, the HIS 11 changes the status about the order to the status indicating that the examination is finished.

Here, there is a demand for resuming the finished examination in order to perform additional imaging. In such a case, radiation imaging for the completed order information can be executed independently of the order from the RIS 12, by issuing instructions for resuming the radiation imaging. The above instructions are performed by the imaging apparatus control unit 5 receiving the operation input from the user received via the imaging apparatus operation unit 3, for example, similarly to the instructions for starting a new radiation imaging. The resumed radiation imaging includes the case where a radiation image is captured again under the same conditions as the already captured radiation image and the case where a radiation image is captured under the different imaging conditions.

If the new radiation imaging is performed, the transmission unit 18, to the HIS 11, transmits the information (the first signal) indicating that the radiation imaging is started. However, if the examination is resumed, it is not allowed to start the re-examination or add imaging afterward with respect to the examination in which the HIS is already notified that the examination is finished. Furthermore, this is the radiation imaging different from the radiation imaging requested by the order issued by the RIS 12, so that an error may occur on the HIS 11. The imaging apparatus control unit 5 precludes the first signal from being transmitted. For example, the imaging apparatus control unit 5 determines whether the order information in which the instruction unit issues start instructions is a new order or an order resumed after the radiation imaging is finished. Such a determination can be made based on the information added to the order information for which the radiation imaging is finished, for example. The imaging apparatus control unit 5 adds such information indicating that radiation imaging is finished at the time of finish. The imaging apparatus control unit 5 regulates the transmission, to the external apparatus, of the first signal indicating that the radiation imaging for the order information is started according to the determination.

Thus, even in the radiation imaging apparatus which receives the order from the RIS 12 to perform imaging, it is possible for the user to perform imaging independently of the order from the RIS 12, while reducing the variance in data with the HIS 11.

Irrespective of a new or a resumed order, the imaging apparatus control unit 5 instructs the X-ray generation apparatus control unit 4 to generate radiation according to the imaging conditions corresponding to the order information. The generated radiation is detected by the X-ray detector 7b to generate a radiation image. The generated radiation image is acquired by the image acquisition unit 21 and displayed on the imaging apparatus display unit 2 by the display control unit 16.

For the added radiation imaging corresponding to the resumed order information, the imaging apparatus control unit 5 adds the information about the resumed order to the radiation image acquired after the completion and transmits the radiation image to the PACS 13.

The example of configuration of the X-ray imaging system has been described above. The configuration illustrated in FIG. 1 is merely an example and may be modified as appropriate. For example, in FIG. 1, the X-ray imaging control apparatus 1 is connected to various apparatuses via the network 15, but the X-ray imaging control apparatus 1 does not necessarily need to be connected to such apparatuses. Even though the network 15 is formed of a wire, the network 15 may be partly formed of a wireless signal transmission path.

In the X-ray imaging system illustrated in FIG. 1, the flow of processing in capturing an X-ray image is described according to an examination flow.

Patient and examination information is input to the X-ray imaging control apparatus 1 according to an examination request form or a request for examination from the RIS 12. The patient information includes a patient name and a patient identification (ID). The examination information includes imaging information defining the contents of imaging applied to the patient.

The imaging apparatus display unit 2 displays a new examination input screen illustrated in FIGS. 2A, 2B, and 2C by the control of the display control unit 16 in the X-ray imaging control apparatus 1. As illustrated in FIG. 2A, the new examination input screen includes a patient information input area 101, a patient information OK button 102, an examination request list 103, a patient information display area 104, an imaging information display area 105, an imaging information input button 106, and an examination start button 107.

The examination request list 103 (a first list) lists examinations received from the RIS 12. As illustrated in FIG. 2C, when any of the examinations is selected from the examination request list 103, patient information (patient ID, patient name, and birth date) corresponding to the selected patient is displayed in the patient information display area 104. An examination ID is displayed in the imaging information display area 105. Imaging information corresponding to the examination ID is displayed immediately beneath the examination ID. As described above, the imaging information is received from the RIS 12. In FIG. 2C, imaging method buttons 109 (a front chest button 109a and a side chest button 109b) corresponding to the imaging information are arranged. According as the imaging information input button 106 is pressed, as illustrated in FIG. 2B, an imaging information input area may be displayed and an imaging method can be added.

The operator confirms patient information and imaging information, and then presses the examination start button 107. This determines an examination to be carried out.

When a new examination is carried out in the imaging apparatus control unit 5, the X-ray imaging control apparatus 1 notifies the HIS 11 that the examination is started. The HIS 11 receives a notification of start of the examination and updates progress information about an examination order.

FIG. 3A illustrates an example of the exemplary embodiment about a past examination display screen 301 on which a past examination list 302 (a second list) is displayed. The past examination list 302 includes the pieces of order information whose radiation imaging is finished, out of the pieces of order information displayed in the examination request list 103 (the first list). The display control unit 16 causes the imaging apparatus display unit 2 to display the past examination list 302 according to operation from the imaging apparatus operation unit 3. Similarly to the examination request list 103, the past examination list 302 arranges an examination ID, a patient (subject) ID, a patient (subject) name, sex, and birth date on one line. If there is a plurality of pieces of information about orders whose examinations are finished, the pieces of information are arranged on a plurality of lines. An examination resumption button 303 is used to select order information whose radiation imaging is to be started again, from the pieces of information about orders whose examinations are finished. When the order information to be resumed is selected via the mouse device or the touch panel of the imaging apparatus operation unit 3 and the examination resumption button 303 is pressed, the imaging apparatus control unit 5 selects the order information for resuming the radiation imaging from the order information arranged in the second list. According as the order information is selected as the resumed order information, the display control unit 16 causes the imaging apparatus display unit 2 to display again the examination request list 103 (the first list) illustrated in FIG. 2A and to display the selected order information in the examination request list 103. The selected order information is added to the end of the examination request list 103, for example.

When input for selecting the resumed order information, which is added to the examination request list 103, is performed via the imaging apparatus operation unit 3, the imaging apparatus control unit 5 functioning as the instruction unit instructs the resumption of the examination and shifts the display on the imaging apparatus display unit 2 to the imaging screen.

At the timing of shifting the screen, if instructions for starting the examination of the order information, which is arranged in the examination request list 103 (the first list) and whose information indicating that the examination is finished (a second signal) is not yet transmitted to the HIS 11, are issued, the transmission unit 18 transmits, to the HIS 11, information (a first signal) indicating that the examination is started. Furthermore, at this point, if instructions for starting the examination of the order information, which is arranged in the examination request list 103 (the first list) and whose information indicating that the examination is finished (the second signal) is not yet transmitted to the HIS 11, are issued, the transmission unit 18 does not transmit, to the HIS 11, information (the first signal) indicating that the examination is started. Thus, internal processing is changed between the resumed and the new examination while performing the shifting to the imaging screen irrespective of the difference between the resumed and the new examination, while reducing the variance in data with the HIS 11.

If the display control unit 16 displays the order information indicating that the radiation imaging is finished in the examination request list 103 (the first list), this makes it easy to perform re-examination. Or, instead of display in the examination request list 103, if the past examination list is displayed in a new examination input screen illustrated in FIG. 2A in which the examination request list 103 is displayed, this also makes it easy to perform re-examination.

On the other hand, it may become difficult to distinguish between examinations already finished and yet to be finished, which sometimes increases the possibility of erroneous operation caused by an inspector. Thus, the display control unit 16 can delete the corresponding order information from the first list of the examination request list 103 according as the transmission unit 18 transmits the second signal and move the order information to the past examination display screen 301 (the second list).

The decision as to whether to delete the order information in which the radiation imaging is finished from the examination request list 103 and shift the order information to the past examination display screen 301 can be set. Such a setting is performed by the imaging apparatus control unit 5 according to the operation input from the imaging apparatus operation unit 3. This allows the user to manage the order information in a desired form.

In the case of re-examination, the X-ray imaging control apparatus 1 does not notify the HIS 11 that the examination is started and stores the re-imaging information. The re-imaging information is stored in a data base as a table illustrated in FIG. 3B. The re-imaging information includes the examination ID for identifying examination, a patient ID for identifying a patient, the number of captured images for indicating the contents of examination, and the number of films.

When the examination start button 107 is pressed, the X-ray imaging control apparatus 1 causes the imaging apparatus display unit 2 to display the imaging screen illustrated in FIG. 4. The imaging screen is a screen used at the time of imaging.

The imaging screen includes a display area basically similar to the new examination input screen described in FIGS. 2A, 2B, and 2C. As illustrated in FIG. 4, newly-added display areas include an image display area 110, a message area 111, an image processing setting area 112, and an examination end button 113.

When the imaging screen is displayed, the imaging method button 109a arranged in the topmost portion in the imaging information display area 105 is selected by default. The X-ray imaging control apparatus 1 causes the imaging apparatus control unit 5 to transmit the imaging conditions (a tube voltage, a tube current, and an irradiation time) set in response to the imaging method button (the imaging method) to the X-ray generation apparatus control unit 4. The imaging apparatus control unit 5 controls the X-ray detector 7 according to the imaging conditions to prepare for imaging.

When preparations are finished, the X-ray imaging control apparatus 1 shifts to a state where the X-ray imaging control apparatus 1 can perform imaging. At this point, the message area 111 displays a message "ready" indicating the state where the X-ray imaging control apparatus 1 can perform imaging.

The operator confirms an imaging method to make settings for imaging and determine the position of a patient. When a series of preparations for imaging is completed, the operator confirms if the X-ray imaging control apparatus 1 is in the state where the X-ray imaging control apparatus 1 can perform imaging, with reference to the message area 111 and then presses an X-ray irradiation switch (not illustrated). The X-ray imaging control apparatus 1 causes the X-ray generation unit 8 to irradiate a subject (the specific region of a patient) with X rays and the X-ray detector 7 to detect the X rays passing through the subject. Thus, the X-ray image is captured.

When the imaging is finished, the X-ray imaging control apparatus 1 causes the imaging apparatus control unit 5 to acquire the captured image from the X-ray detector 7 and to subject the acquired captured image to an image processing based on predetermined image processing conditions. The predetermined image processing conditions are previously defined according to the imaging method.

When the image processing is finished, the X-ray imaging control apparatus 1 displays the captured image subjected to the image processing in the captured image display area 110. If the operator wants to change the contrast or other settings of the captured image, for example, the operator operates a button for contrast or luminance provided in the image processing setting area 112. This allows the operator to apply an additional image processing to the captured image displayed in the captured image display area 110. When the operator presses the imaging method buttons 109, the imaging conditions and the image processing conditions for the image are stored and the next imaging is started.

The operator repeats the above procedures to perform imaging according to all imaging methods in the imaging information display area 105. When all imaging operations are finished, the operator presses the examination end button 113. This ends a series of examinations. The X-ray imaging control apparatus 1 displays again a search condition input screen. At this point, the X-ray imaging control apparatus 1 causes the imaging apparatus control unit 5 to output a captured image or examination information to the PACS 13, a printer 14, or the ROM of each apparatus, for example. In the RIS 12 or the ROM, the captured image is stored in association with patient information.

The X-ray imaging control apparatus 1 causes the imaging apparatus control unit 5 to notify the HIS 11 that the examination is finished, for the case of a new examination. When the HIS 11 is notified that the examination is finished, the HIS 11 updates progress information of the examination order. For the case of a re-examination, the imaging apparatus control unit 5 updates re-imaging information and notifies the HIS 11 thereof.

For the finished examination, "done" is written in an examination state column in the examination request list 103.

Figure 5:
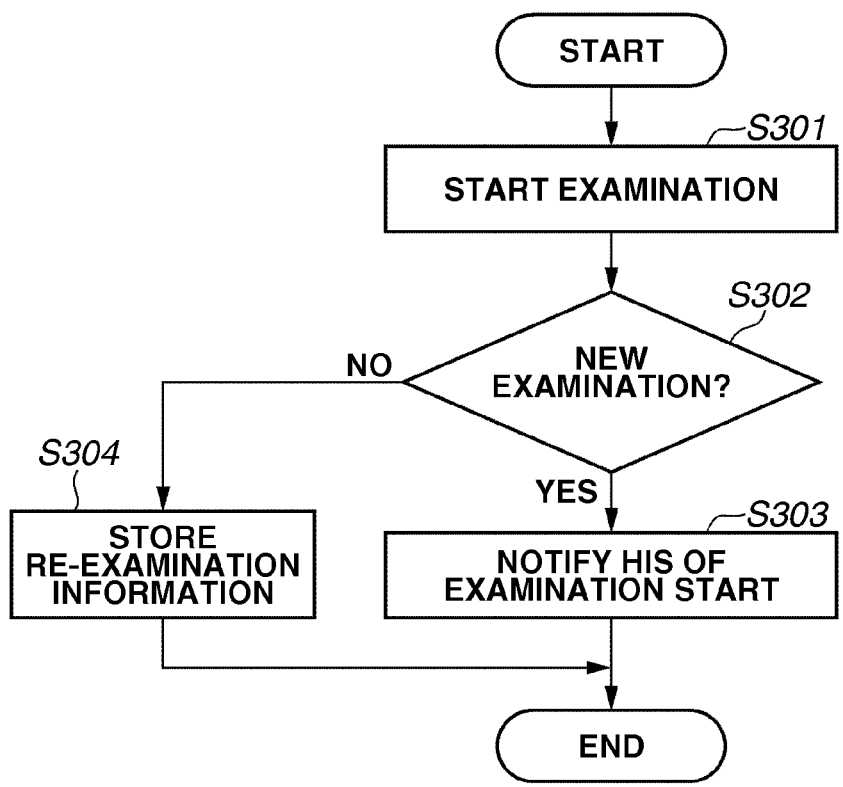
FIG. 5 is a flow chart according to the first exemplary embodiment.

The operation of the X-ray imaging system at the time of starting the examination according to the present exemplary embodiment is described below with reference to a flow chart in FIG. 5.

In step S301, the imaging apparatus control unit 5 is instructed to start the examination. In step S302, the imaging apparatus control unit 5 confirms if the instructed examination is a new examination. If the examination is a new one (YES in step S302), then in step S303, the imaging apparatus control unit 5 notifies the HIS 11 of the start of the examination. If the examination is a re-examination (NO in step S302), then in step S304, the imaging apparatus control unit 5 stores re-examination information in a database.

Figure 6:
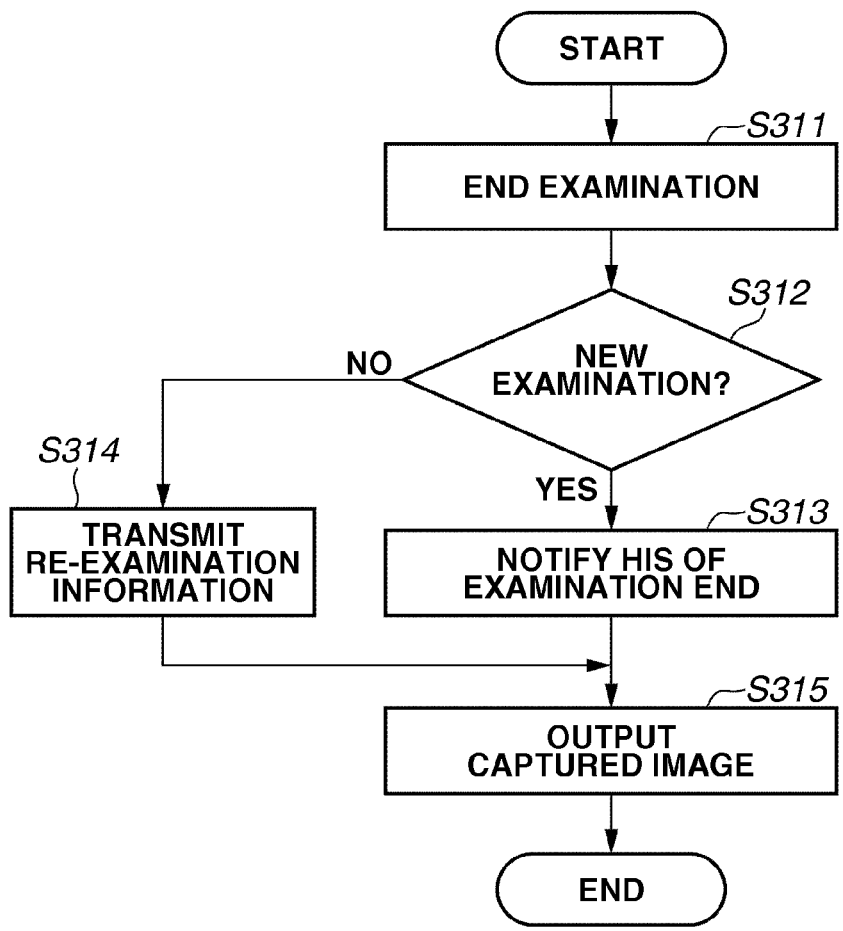
FIG. 6 is a flow chart according to the first exemplary embodiment.

Next, the operation of the X-ray imaging system at the time of finishing the examination according to the present exemplary embodiment is described below with reference to a flow chart in FIG. 6.

In step S311, the imaging apparatus control unit 5 is instructed to finish the examination. In step S312, the imaging apparatus control unit 5 confirms if the instructed examination is a new examination. If the examination is a new one (YES in step S312), then in step S313, the imaging apparatus control unit 5 notifies the HIS 11 of the end of the examination. If the examination is a re-examination (NO in step S312), then in step S314, the imaging apparatus control unit 5 transmits re-examination information to the HIS 11. In step S315, the imaging apparatus control unit 5 outputs a captured image to the PAC 13. At this point, the image captured in the re-examination is output with re-examination information provided in an image header, for example, as supplemental information.

A second exemplary embodiment of the present invention is described below. In the first exemplary embodiment, an example of switching the notification method of implementation information according to the implementation achievement of the examination has been described. In a second exemplary embodiment, there is described a case where a purpose for starting re-examination is selected and the notification method of implementation information is switched according to the selection.

Figure 7:
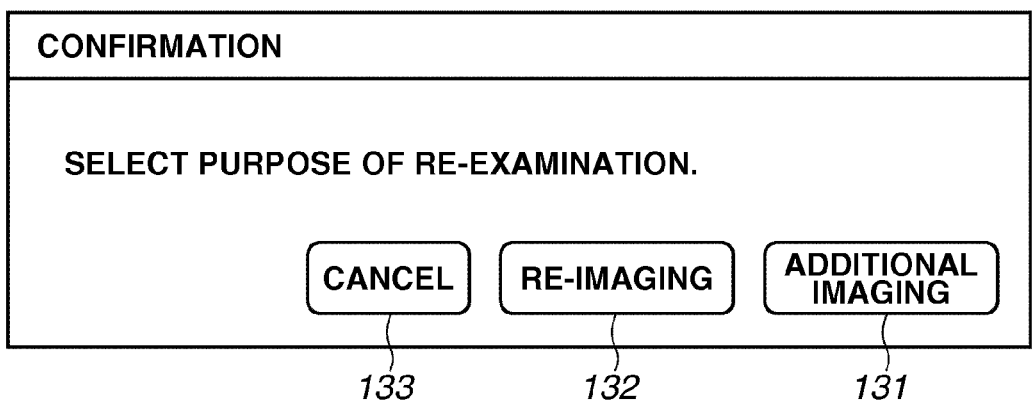
FIG. 7 is an example of a dialog for confirming the purpose of re-examination according to a second exemplary embodiment of the present invention.

Assuming that an instruction for starting an examination for a finished examination listed in the examination request list 103 is issued via the new examination input screen illustrated in FIGS. 2A, 2B, and 2C. The imaging apparatus control unit 5 displays a dialog for confirming the purpose of re-examination as illustrated in FIG. 7. An additional imaging button 131 is used to issue instructions for additional imaging in the finished examination. A re-imaging button 132 is used to treat the imaging of the finished examination as an imaging error and issues instructions for re-imaging. The above purpose of re-examination is held by the imaging apparatus control unit 5 until the re-examination is finished.

The imaging apparatus control unit 5 displays the imaging screen on the imaging apparatus display unit 2, and the X-ray imaging control apparatus 1 shifts to a state where the X-ray imaging control apparatus can perform imaging.

Figure 8:
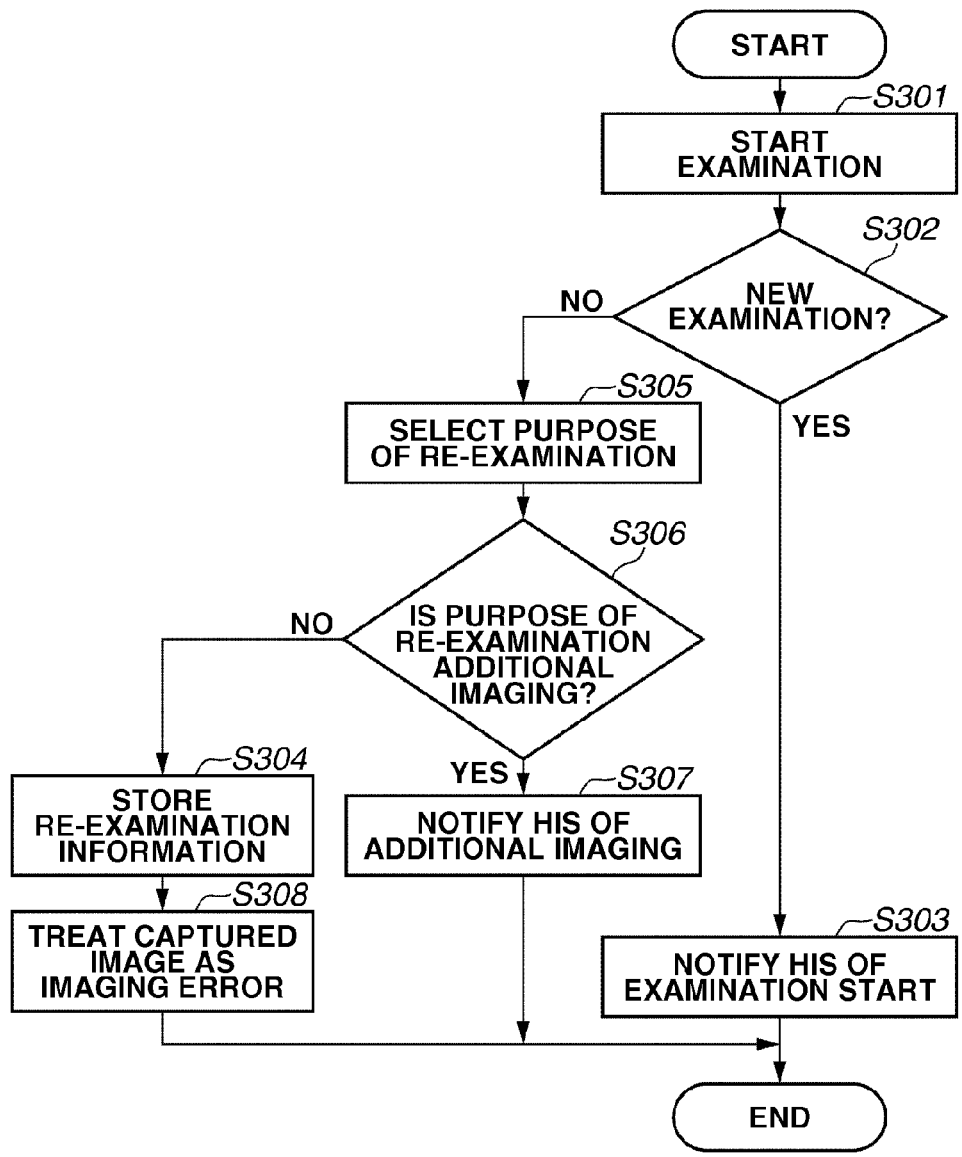
FIG. 8 is a flow chart according to the second exemplary embodiment.

The operation of the X-ray imaging system at the time of starting the examination according to the present exemplary embodiment is described below with reference to a flow chart in FIG. 8.

Steps S301 and S303 are similar to those in the first exemplary embodiment, so that the description thereof is omitted. In step S302, if instructions are determined as those for the re-examination (NO in step S302), then in step S305, the dialog for confirming the purpose of re-examination is displayed. In step S306, the purpose of re-examination is confirmed. If the purpose of re-examination is the additional imaging (YES in step S306), then in step S307, the HIS 11 is notified of the start of additional imaging. If the purpose of re-examination is the re-imaging (NO in step S306), then in step S304, the imaging apparatus control unit 5 stores information about re-examination in the database. In step S308, the captured image of the examination to be re-examined is treated as an imaging error.

Figure 9:
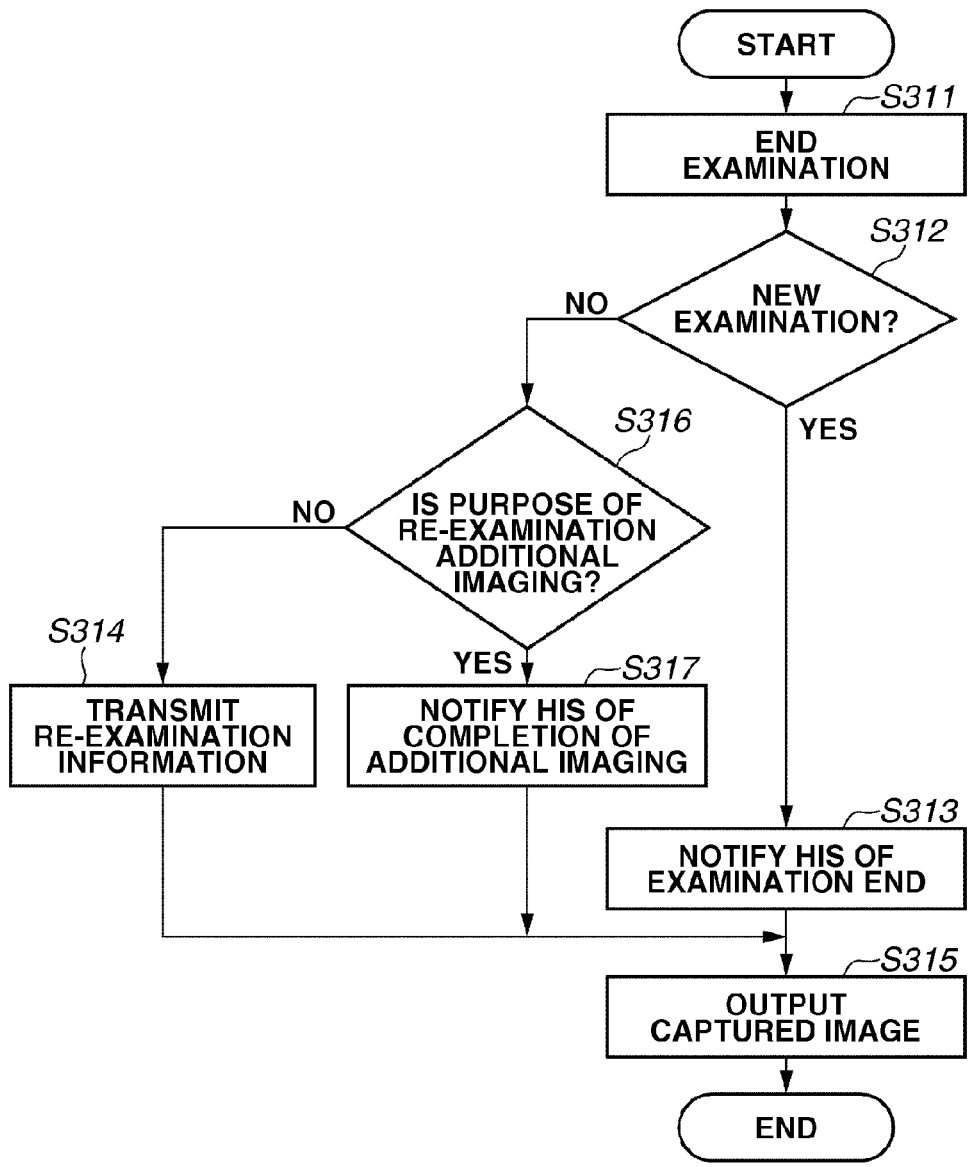
FIG. 9 is a flow chart according to the second exemplary embodiment.

The operation of the X-ray imaging system at the time of finishing the examination according to the present exemplary embodiment is described below with reference to a flow chart in FIG. 9.

Steps S311 and S313 are similar to those in the first exemplary embodiment, so that the description thereof is omitted. In step S312, if instructions are determined as those for the re-examination (NO in step S312), then in step S316, the purpose of re-examination stored at the time of starting the examination is confirmed. If the purpose of re-examination is additional imaging (YES in step S316), then in step S317, the HIS 11 is notified that the additional imaging is completed. If the purpose of re-examination is re-imaging (NO in step S316), the imaging apparatus control unit 5 transmits re-examination information to the HIS 11. The HIS 11 which receives the re-examination information identifies the re-examined examination from the re-examination information to update account information. In step S315, the image captured in the re-examination is output to the PACS 13 and the printer 14. The captured image treated as an imaging error in step S308 is provided with imaging error information and output to the PACS 13.

A third exemplary embodiment of the present invention is described below. The system configuration of the third exemplary embodiment is similar to the one that is illustrated in FIG. 1, so that the description thereof is omitted. The points different from those of the above exemplary embodiments are mainly described.

Figure 10:
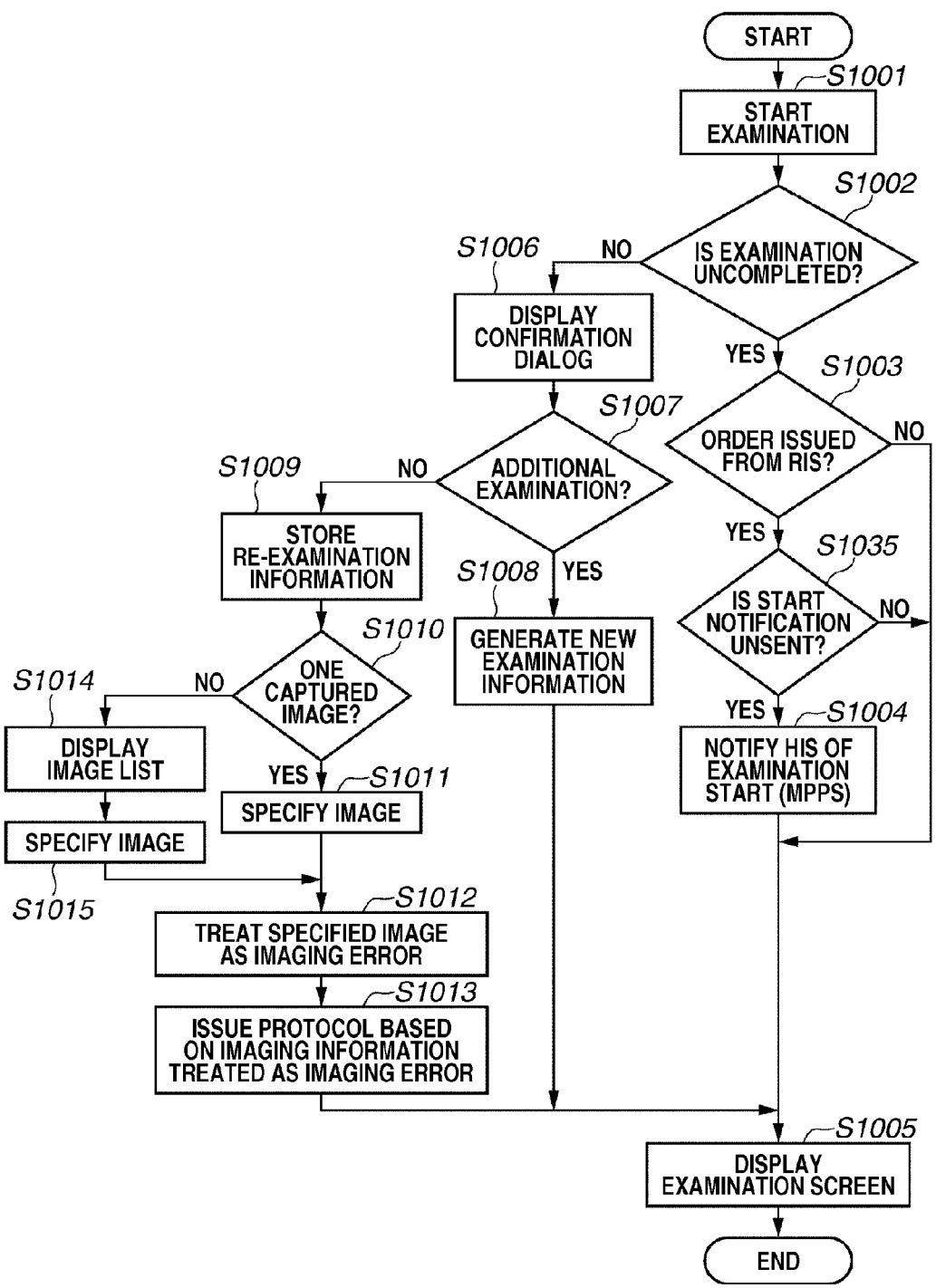
FIG. 10 is a flow chart illustrating a flow of processing at the time of starting examination according to a third exemplary embodiment of the present invention.

The flow of processing performed by the X-ray imaging control apparatus 1 according to the present exemplary embodiment is described below with reference to a flow chart in FIG. 10. In FIG. 10, processing is described in a case where a selection screen for examination illustrated in FIG. 2B is displayed on the imaging apparatus display unit 2, and the examination start button 107 is pressed by operation input via the imaging apparatus operation unit 3.

In step S1001, the imaging apparatus control unit 5 determines that the examination start button 107 is pressed. In response to that, the imaging apparatus control unit 5 recognizes that the imaging apparatus control unit 5 is instructed to start the examination and stores, in the memory, the information indicating that the imaging apparatus control unit 5 is instructed to start the examination.

In step S1002, the imaging apparatus control unit 5 determines whether the examination selected by pressing the examination start button 107 is finished (completed) or not finished (uncompleted). The term "new examination" refers to an examination that the transmission unit 18 has not transmitted, to the HIS 11, a notification indicating that the examination is finished based on specifications of a Modality Performed Procedure Step (MPPS). Alternatively, the term "new examination" refers to an examination that the transmission unit 18 has transmitted, to the HIS 11, a notification that the examination is finished, but the reception unit 17 has not yet received an acknowledgement from the HIS 11. Whether an examination is a new examination is not determined based on whether a notification of the examination start has been made. The term "finished examination" refers to an examination that the transmission unit 18 has transmitted, to the HIS 11, a notification indicating that the examination is finished based on specifications of the MPPS and the reception unit 17 has received the acknowledgement from the HIS 11. Flag information indicating whether the transmission of the above notification that the examination is finished is stored in the memory of the imaging apparatus control unit 5. A determination is made as to whether the examination is finished or not finished with reference to the flag information.

In step S1003, the imaging apparatus control unit 5 determines whether the selected examination corresponds to the imaging order placed by the RIS 12 or by the imaging apparatus control unit 5. For example, for the case where the imaging order which is generated by inputting data in the patient information input area 101 and pressing the patient information OK button 102 illustrated in FIG. 2A or 2B, it is determined that the examination does not correspond to the imaging order placed by the RIS 12 (NO in step S1003). An examination ID of StudyInstance UID, for example, is used for identifying an order source. As indicated in the examination screen illustrated in FIGS. 2A and 2B, the examination whose examination ID starts with "O" is determined as the imaging order (examination) received from the RIS 12. The examination whose examination ID starts with "M" is determined as the imaging order placed by the imaging apparatus control unit 5 (modality).

If the examination corresponds to the imaging order which the reception unit 17 receives from the RIS 12 (YES in step S1003), the processing proceeds to step S1004.

In step S1035, the imaging apparatus control unit 5 determines whether a notification indicating that the examination of the selected examination is started is transmitted to the HIS 11. Completion flag information is stored in the memory of the imaging apparatus control unit 5 according as the transmission of a notification of the HIS 11 that the examination is started is completed. A determination is made with reference to the completion flag information. If the notification indicating the start of the examination is not transmitted (unsent) to HIS 11 (YES in step S1035), the processing proceeds to step S1004.

In step S1004, the transmission unit 18 transmits, to the HIS 11, a notification of the examination start based on the MPPS specification, with respect to an examination corresponding to the order placed by the RIS 12 whose notification of the examination start is not transmitted. In this case, the notification of the examination start may be transmitted to the RIS 12 or an integrated apparatus in which the HIS 11 is integrated with the RIS 12 if such a integrated apparatus is used. A transmission destination is set as appropriate according to a system in use.

In step S1035, if it is determined that the notification of the examination start is transmitted (sent) to the HIS (NO in step S1035), a re-notification is to be regulated. Such regulation is realized by the imaging apparatus control unit 5 executing processing in step S1035.

In step S1005, the display control unit 16 causes the imaging apparatus display unit 2 to display the examination screen corresponding to the selected examination. An examination start screen is illustrated in FIG. 4, for example. If there is no relevant captured image at the time of starting the examination, an X-ray image is not displayed in the image display area on the left in FIG. 4.

For the examination whose order is placed by the modality, the region to be examined is sometimes unspecified. In this case, the display control unit 16 displays the examination screen after an imaging method list displaying screen, for example, illustrated in FIG. 2C is displayed.

In step S1002, if the imaging apparatus control unit 5 determines that the examination is not uncompleted (NO in step S1002), the processing proceeds to step S1006. In step S1006, the display control unit 16 causes the imaging apparatus display unit 2 to display a dialog for confirmation. For example, the dialog for confirmation is a window illustrated in FIG. 7 which displays the instruction message "Select the purpose of examination," an additional imaging button 131, and a re-imaging button 132.

As illustrated in FIG. 7, if a cancel button is displayed, the start of examination is cancelled according as the cancel button is pressed, and the display control unit 16 keeps displaying the screen illustrated in FIG. 2A or 2B.

If the processing proceeds to step S1006, the selected examination is once completed. Selecting such a once-completed examination to start (resume) the examination seems to have at least two cases.

A first case refers to a situation where an additional diagnosis needs to be made in addition to an initially-presumed diagnosis using a captured image and thus, an additional imaging is required. In this case, another imaging is performed and new account processing about the additional imaging is required. This is because an additional expenses corresponding to the additional diagnosis can be charged. Therefore, it is necessary to notify the HIS 11 of the additional imaging information.

A second case refers to a situation where, although the examination is completed, an X-ray image is not suited for diagnosis and thus, re-imaging is required. In this case, a new image needs to be captured. However, this case is inapplicable to imaging for which the HIS 11 is notified of the implementation information to generate new account processing. In this case, although X-ray imaging is performed and an image is transmitted to the PACS, it is not appropriate to charge for expenses by placing a new imaging order, so that the new account processing performed by the HIS 11 is not required or may be prohibited.

The processing in step S1007 and the subsequent steps is conducted to support the above two cases.

In step S1007, the imaging apparatus control unit 5 determines whether instructions for the resumption of the examination are issued. As described above, if the additional imaging button 131 displayed in the dialog for confirmation is pressed by operation input to the imaging apparatus operation unit 3, the imaging apparatus control unit 5 determines that instructions for additional examination are issued. This corresponds to processing for determining the above first situation. In this case (YES in step S1007), the processing proceeds to step S1008.

In step S1008, the imaging apparatus control unit 5 generates new examination information corresponding to the additional examination. The new examination information is associated with an examination ID different from that of the completed examination which is selected when the additional examination is instructed. Since the order of the examination is placed by the modality side, an examination ID starting with "M" is generated. The new examination information is stored in the memory of the imaging apparatus control unit 5. After the processing in step S1008 is finished, the processing proceeds to step S1005. The display control unit 16 displays the examination screen corresponding to the newly-generated examination information.

In step S1007, if the re-imaging button 132 displayed in the dialog for confirmation is pressed by operation input to the imaging apparatus operation unit 3, the imaging apparatus control unit 5 determines that instructions for the resumption of the examination are issued. This corresponds to processing for determining the above second case. In this case (NO in step S1007), the processing proceeds to step S1009. It is assumed that there is an X-ray image which is not suited for diagnosis, and therefore, in the following processing, the X-ray image is treated as an imaging error and a processing for issuing new imaging information (protocol) is performed based on the imaging conditions for the X-ray image treated as the imaging error.

In step S1009, the imaging apparatus control unit 5 associates information indicating that the examination is resumed with the selected completed examination and stores the information in the memory. The following describes the examination with the examination ID of O006.

In step S1010, the imaging apparatus control unit 5 determines whether the number of captured images corresponding to the examination ID of the selected completed examination is one or more than one. The determination is made based on the number of the X-ray images associated with the examinations whose examination ID corresponds to O006. If the imaging apparatus control unit 5 determines that the captured image is one (YES in step S1010), the processing proceeds to step S1011. The number of the X-ray images may not include the number of the X-ray images determined as imaging errors, i.e., determined as failure in imaging.

In step S1011, the imaging apparatus control unit 5 specifies the single X-ray image associated with the examination ID. In step S1012, the imaging apparatus control unit 5 associates the information indicating that the specified X-ray image is treated as the imaging error and stores the specified X-ray image in the memory. In step S1013, the imaging apparatus control unit 5 issues new imaging information (protocol) based on the imaging conditions for the X-ray image treated as the imaging error. The protocol may include additional information as well as information at least about an imaging method, an imaging target region, and an imaging direction. The issued protocol information is stored in the memory.

If the imaging apparatus control unit 5 determines that a plurality of images is associated with the examination whose examination ID is O006 (NO in step S1010), the processing proceeds to step S1014. In step S1014, the display control unit 16 displays the list of the X-ray image data associated with the examination ID of O006. The list displays the thumbnail image of the X-ray image data and imaging information related to each image. In step S1015, a single or a plurality of the X-ray images treated as the imaging error is specified according to the operation input from the imaging apparatus operation unit 3. Thereafter, as described above, the specified X-ray image is subjected to processing in steps S1012 and S1013 to issue a corresponding protocol.

For the case of the first case, if the order of the examination is placed by the modality, there is a possibility that the order of the corresponding examination is placed by the RIS 12, so that the imaging apparatus control unit 5 performs control not to output a notification of examination start based on the MPPS at the time of starting the examination.

For the case of the second case, if the finished examination is resumed, the imaging apparatus control unit 5 performs control to start the examination without making the notification to the HIS 11. This prevents the HIS 11 from executing account processing corresponding to notification based on the MPPS. Furthermore, an error caused by the MPPS issuing a processing for starting the examination which corresponds to the completed examination can be reduced.

In the third exemplary embodiment, if an additional examination is required in relation to an examination, a new examination order is placed in view of the IHE framework and account processing. In this case, an examination ID (StudyInstance UID) is separately provided in each examination, so that the PACS handles examinations as different ones. This may make diagnosis complicated. Therefore, according to a fourth exemplary embodiment of the present invention, relevant information indicating association between examinations is provided for the additional examination to make it easy to refer to a plurality of examinations on the PACS side.

Figure 11:
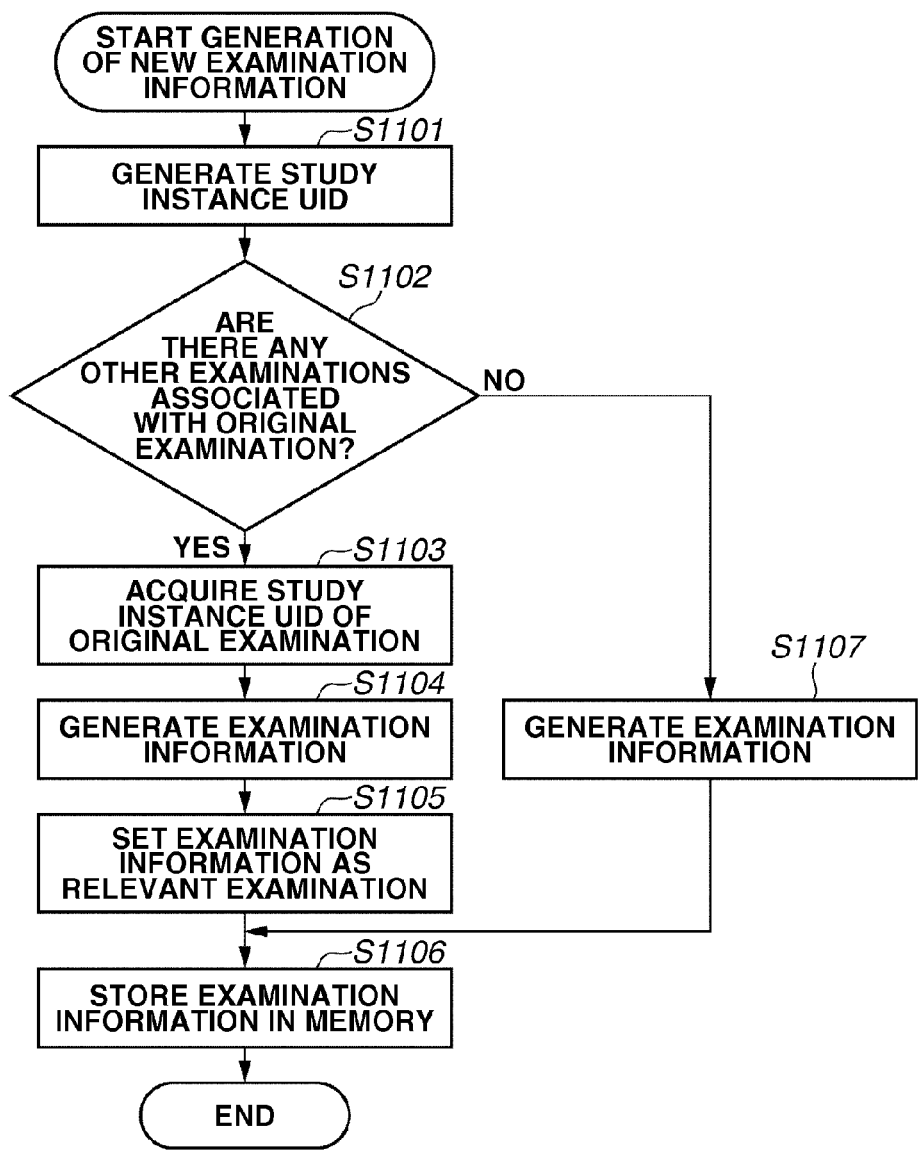
FIG. 11 is a flow chart illustrating a flow of information generation processing for a new examination according to a fourth exemplary embodiment of the present invention.
Figure 12:
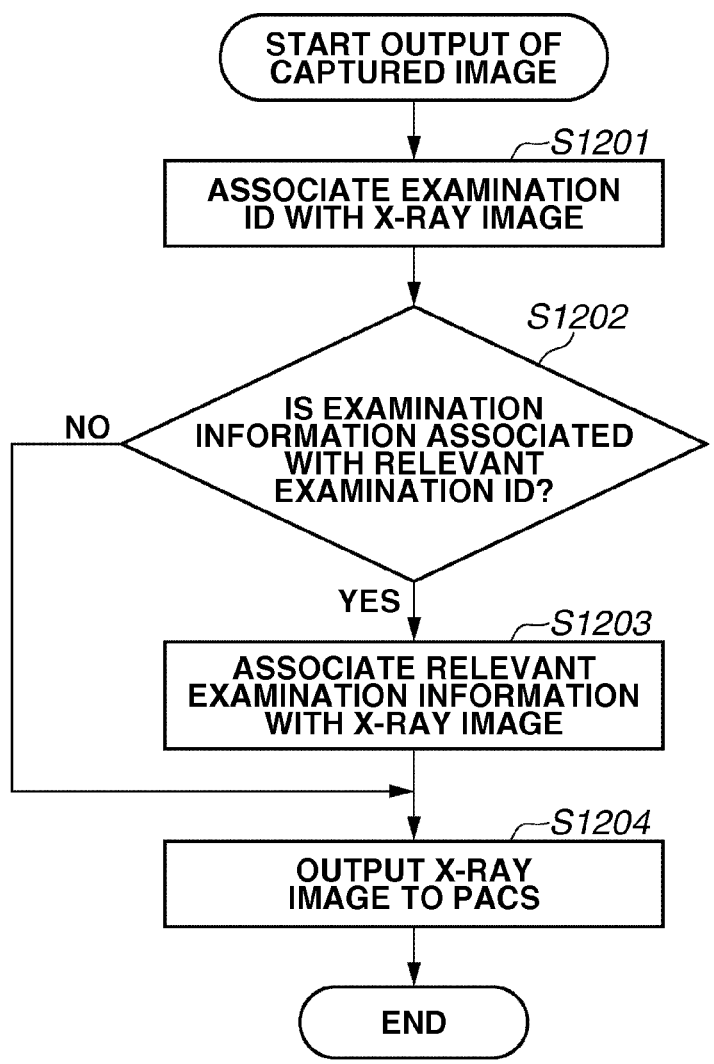
FIG. 12 is a flow chart illustrating a flow of output processing for a captured image according to a fourth exemplary embodiment of the present invention.

The fourth exemplary embodiment is described below with reference to FIGS. 11 and 12. A system configuration is similar to the one in FIG. 1, so that the description thereof is omitted. FIG. 11 is a flow chart illustrating a detailed processing in generating information for a new examination in step S1008 in FIG. 10, for example.

In step S1101, the imaging apparatus control unit 5 generates a new examination ID (StudyInstance UID) corresponding to an additional examination. The examination ID is the one that unique three-digit numerals, for example, are provided with the character "M" indicating modality controlled by the imaging apparatus control unit 5. Herein, the generated examination ID is to be M001.

In step S1102, the imaging apparatus control unit 5 determines whether there are other examinations to be associated with the examination of M001. For example, if instructions for the start of the examination are issued with the examination of M001 selected in step S1001 described in FIG. 10, the imaging apparatus control unit 5 determines the examination of M001 to be a relevant examination. For example, if the order of a new examination is placed by inputting data to the patient input screen illustrated in FIG. 2A, the imaging apparatus control unit 5 determines that there is no relevant examination. If the imaging apparatus control unit 5 determines that there is a relevant examination as described above, the display control unit 16 is caused to display a graphic user interface (GUI) for receiving approval as to whether the examination of M001 may be associated with the examination of O006 or a GUI for selecting an examination associated with M001 from a list displaying examinations other than O006 This can secure the setting of relevant examinations. The imaging apparatus control unit 5 performs the setting as to whether the GUI is displayed and stores the setting information in the memory, and the display control unit 16 switches the display of the GUI to on or off with reference to the setting information, thereby reducing the user's operational burden of operation as appropriate.

If the imaging apparatus control unit 5 determines that there are relevant examinations (YES in step S1102), the processing proceeds to step S1103. If the imaging apparatus control unit 5 determines that there are no relevant examinations (NO in step S1102), the processing proceeds to step S1107.

If the imaging apparatus control unit 5 determines that there are relevant examinations, then in step S1103, the imaging apparatus control unit 5 acquires the examination ID (StudyInstance UID) of the relevant examination from the memory.

In step S1104, the imaging apparatus control unit 5 generates examination information. The examination information includes patient information such as ID of a patient as a subject and a patient name, imaging information such as the number of captured images and imaging target regions, and information about output format as to whether to perform image processing and film output, for example. In step S1105, the imaging apparatus control unit 5 associates the information about the examination ID acquired in step S1103 with the generated examination information. Specifically, the examination ID is included as relevant examination information in the generated examination information.

In step S1106, the imaging apparatus control unit 5 stores the examination information including the relevant examination information in the memory.

On the other hand, if the imaging apparatus control unit 5 determines that there are no relevant examinations, the processing proceeds to step S1107, and the imaging apparatus control unit 5 generates examination information as is the case with step S1104. Here, the processing for generating information about the new examination is ended.

The processing for associating the relevant examination information with the examination information may be carried out at the time of imaging or outputting an image to the PACS 13 as well as at the time of generating a new examination information.

The processing for outputting a captured image to the PACS 13 is described below with reference to FIG. 12. It is assumed that the captured image is acquired by imaging corresponding to the examination information generated based on the processing described in FIG. 11.

In step S1201, the imaging apparatus control unit 5 associates the examination ID with the X-ray image with reference to the examination information. Specifically, the imaging apparatus control unit 5 embeds the relevant examination ID in the header portion of the Digital Imaging and Communications in Medicine (DICOM) image.

In step S1202, the imaging apparatus control unit 5 determines whether the relevant examination ID is associated with the X-ray image with reference to the examination information. If the relevant examination ID is associated therewith (YES in step S1202), the processing proceeds to step S1203. In step S1203, the imaging apparatus control unit 5 associates the relevant examination information with the X-ray image. Specifically, the imaging apparatus control unit 5 embeds the relevant examination ID in the header portion of the DICOM image. If the imaging apparatus control unit 5 determines that there is no relevant examination (NO in step S1202), the relevant examination ID is not associated therewith.

In step S1204, the transmission unit 18 transmits the X-ray image to the PACS 13.

The above processing makes it easy for the user to refer to a plurality of examinations by executing the processing with reference to the relevant examination information on the side of the PACS 13. For example, if one of the relevant information and the main examination is selected with reference to the relevant examination information associated with the X-ray image, the PACS 13 changes a frame or display color of the other one of the relevant information and the main examination to change the display mode, so that the correlation of a plurality of examinations can be displayed on the display unit in an easily understood manner. Alternatively, the relevant information and the main examination are displayed side by side to make it easy to refer to a plurality of examinations.

The processing in steps S1201 to S1203 may be performed when the X-ray image is captured and an image with the DICOM format is generated instead of performing after instructions for the output of the captured image are issued.

In the present exemplary embodiment, the examination ID as the relevant examination information is associated with the one examination, but the exemplary embodiment is not limited thereto. For example, an examination group ID shared between one examination and the other examination is stored in an associated manner, and thus the similar purpose can be achieved by using the examination group ID.

A fifth exemplary embodiment of the present invention describes an example in which a part of information among the pieces of the implementation information about the resumed examinations is transmitted to an external apparatus and a part of information is not transmitted. For example, dosage information can be included in the implementation information prescribed by the MPPS. If the HIS manages the dosage of each patient, information about dosage is desirably received irrespective of account processing, so that the processing supporting the above is performed.

Figure 13:
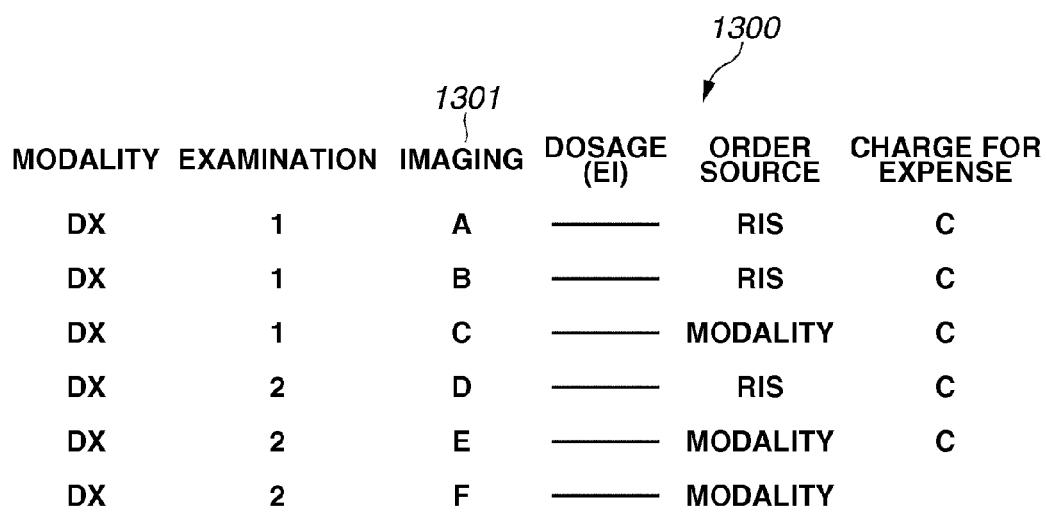
FIG. 13 illustrates a format of dosage information according to a fifth exemplary embodiment of the present invention.

A format example of dosage information 1300 transmitted to the HIS 11 is illustrated in FIG. 13. The dosage information 1300 includes a dosage list 1301, a subject name 1302 such as a patient name, and a total dosage information 1303, for example. The dosage list 1301 stores information as lists such as "modality" used for imaging, "examination" or examination ID indicating an examination unit, "imaging" indicating an imaging unit such as a still image or fluoroscopic image, "dosage" represented by a Reached Exposure Index (REX) value or an exposure index (EI) value, "order source," and information as to whether to charge costs.

In the example illustrated in FIG. 13, the modality is denoted by "DX" (still image imaging modality), the examination unit is expressed by "1" or "2," the imaging is represented by "A" to "F," an order source by which an imaging order is placed is signified by "RIS" or "modality," and the information as to whether to charge costs is indicated by "C" which means that costs are charged and a blank which means that costs are not charged. The list provides the number of captured images and how much dosage is irradiated for each imaging. The list clarifies whether the order is placed by the RIS 12 or the imaging apparatus (modality).

The total dosage information 1303 includes information about a total dosage range indicating the level of the total dosage and a total dosage range in each examination, for example. Alternatively, one of the above pieces of information may be included. The total dosage may be included as is. Considering a case where such information is given to a subject, the dosage may be displayed by EI ranges such as 1 to 10, 10 to 100, or 100 to 1000, to allow the dosage to be easily understood. Furthermore, a deviation index (DI) which is a deviation of the EI is included to provide a difference from a standard dosage. Still furthermore, it is useful to display a targeted value of the EI.

The dosage information 1300 is updated appropriately every time imaging is performed and the dosage is specified, and the updated dosage information is stored in the memory.

The flow of processing about the transmission of implementation information is described below based on a flow chart in FIG. 14. The processing in FIG. 14 indicates the flow of the processing in pressing the examination end button 113 in FIG. 4 to issue instructions for ending the examination, for example.

In step S1401, the imaging apparatus control unit 5 detects that the examination end button 113 illustrated in FIG. 4 is pressed and issues instructions for ending the examination. In step S1402, the imaging apparatus control unit 5 determines whether the ended examination is a new examination. As is the case with step S1002 in FIG. 10, the determination is made based on whether the examination for which the notification of the examination end is transmitted to the HIS 11. If the imaging apparatus control unit 5 determines that the examination is a new examination (YES in step S1402), the processing proceeds to step S1403. If the end notification is already transmitted to the HIS 11 (NO in step S1402), the processing proceeds to step S1408.

In step S1403, the imaging apparatus control unit 5 determines whether the examination is performed based on the imaging order placed by the RIS. The determination processing is also similar to that in step S1003 in FIG. 10. If the imaging apparatus control unit 5 determines that the examination is performed based on the order placed by the RIS (YES in step S1403), the processing proceeds to step S1404. If the imaging apparatus control unit 5 determines that the examination is not performed based on the order placed by the RIS (NO in step S1403), i.e., for example, if the examination is performed based on the order placed by the modality, the processing proceeds to step S1407.

In step S1404, the transmission unit 18 notifies the HIS 11 that the examination is ended based on specifications of the MPPS, for example.

In step S1407, since the examination corresponds to the order placed by the modality, the transmission unit 18 does not transmit, to the HIS 11, the notification of the examination start based on specifications of the MPPS until the examination is ended, in consideration of the case where the processing for combining with the imaging order placed later by the RIS 11 is carried out. Then, at the time when the examination is ended, the transmission unit 18 transmits, to the HIS 11, the notification of the examination start. In this case, in step S1404, the notification of the examination end follows.

In step S1405, the transmission unit 18 transmits the dosage information 1300 to the HIS 11. If the transmission unit 18 transmits, to the HIS 11, the dosage information 1300 combined with the notification of the examination end performed in step S1404, a communication processing is further simplified.

In step S1406, the transmission unit 18 outputs the X-ray image captured in the examination to the PACS 13.

In step S1402, if the imaging apparatus control unit 5 determines that the examination is not a new examination (NO in step S1402), the processing proceeds to step S1408. In step S1408, the imaging apparatus control unit 5 associates the information indicating that the resumed examination is finished again with the examination, and stores the associated information in the memory. This means that the information indicating the resumption of the examination is associated with the information indicating the completion of the resumed examination. Thereafter, in step S1405, the transmission unit 18 transmits the dosage information 1300 to the HIS 11.

If the processing proceeds from step S1402 to step S1408, information indicating that the examination is ended is not transmitted outside the apparatus. This processing is performed to prevent an error from occurring in the HIS 11 because of the transmission of the information about the end of the once-completed examination.

The processing in FIGS. 10 and 14 is executed by not transmitting, to the HIS 11, the notification of the start and end of the once-completed examination. This allows reducing an error in the HIS 11 caused by notifying the HIS 11 of the implementation information about the once-completed examination. On the other hand, the dosage information is output to the HIS 11 to allow appropriately managing the dosage of the subject.

The present exemplary embodiment is described above on the assumption that the dosage information is transmitted to the HIS 11. However, the dosage information may be transmitted to a dedicated server for managing the dosage, the RIS 12, or the PACS 13 as well as the HIS 11.

The present invention may have various exemplary embodiments in a system, an apparatus, a method, a program, and storage medium. Specifically, the present invention may be applied to a system formed of a plurality of devices or an apparatus formed of one device.

The present invention may be realized as software having a program realizing the above exemplary embodiments such that the program is installed in one or a plurality of computers and executed by the CPU of the computers. In this case, the program includes a program code for causing the computer to execute each processing illustrated in the flow charts in FIGS. 5 to 12 and FIG. 14.

The computer executes the read program to realize the functions of the above exemplary embodiments or may realize the functions of the exemplary embodiments based on the instructions of the program in collaboration with an operating system (OS) operating on the computer. In this case, the OS performs a part or all of the actual processing to realize the functions of the above exemplary embodiments.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the embodiments of the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-135832 filed Jun. 15, 2012, which is hereby incorporated by reference herein in its entirety.

What is claimed is:

1. A radiation imaging control apparatus comprising:
   a reception unit configured to receive information corresponding to a radiation order for radiation imaging;
   a transmission unit configured to transmit information indicating a first state of a radiation order, in which corresponding radiation imaging is started but not finished, and to transmit information indicating a second state of the radiation order, in which corresponding radiation imaging is finished; and
   a control unit configured to limit a transmission of information indicating the first state of the radiation order, in a case where an instruction is issued for re-starting radiation imaging corresponding to the radiation order after the information indicating the second state of the radiation order has been transmitted.

2. The radiation imaging control apparatus according to claim 1, wherein
   the reception unit is configured to receive information corresponding to radiation orders for radiation imaging; and
   the radiation imaging control apparatus further comprising:
   a display control unit configured to cause a display unit to display a first list including the received information and a second list including information of a radiation order of the radiation orders for which the information indicating the second state has been transmitted; and
   a selection unit configured to select a radiation order in the second list;
   wherein the display control unit is configured to cause the display unit to display the selected order information in the first list, in response to a selection of the selection unit.

3. The radiation imaging control apparatus according to claim 2, further comprising:
   an instruction unit configured to issue an instruction for starting radiation imaging for the radiation order in the first list;
   wherein the transmission unit is configured to transmit the information indicating the first state to an external device in a case where the instruction unit issues an instruction for starting radiation imaging for the radiation order in the first list, for which the information indicating the second state has not been transmitted, and
   wherein the transmission unit is configured to not transmit information indicating the first state to the external device in a case where the instruction unit issues an instruction for starting radiation imaging for the radiation order in the first list, for which the information indicating the second state has been transmitted.

4. The radiation imaging control apparatus according to claim 3, wherein the control unit is configured to, in response to an issuance of an instruction for starting radiation imaging for the radiation order, resume radiation imaging for radiation order in the first list, having moved from the second list to the first list.

5. The radiation imaging control apparatus according to claim 3, wherein the display control unit is configured to, in response to an issuance of an instruction for starting radiation imaging for the radiation order, display an imaging screen for starting radiation imaging.

6. The radiation imaging control apparatus according to claim 2, wherein, in response to a transmission of the information indicating the second state, the display control unit is configured to delete the corresponding radiation order from the first list and to add the radiation order to the second list.

7. The radiation imaging control apparatus according to claim 2, further comprising:
a setting unit configured to set, in response to the transmission of the information indicating the second state, whether to delete the corresponding radiation order from the first list and to add the radiation order to the second list.

8. The radiation imaging control apparatus according to claim 1, further comprising:
an acquisition unit configured to acquire a radiation image from a radiation detector based on an imaging condition corresponding to the radiation order,
wherein the transmission unit is configured to transmit the radiation image together with information as to whether the radiation imaging corresponding to the acquired image has been re-started.

9. The radiation imaging control apparatus according to claim 8, wherein the transmission unit is configured to transmits information about the re started radiation imaging to an external device, in response to completion of the re-started radiation imaging.

10. The radiation imaging control apparatus according to claim 1,
wherein the reception unit is configured to receive information from a departmental radiation information system,
wherein the transmission unit is configured to transmit the information indicating the first state and the information indicating the second state to a hospital information system, and
wherein the transmission unit is further configured to transmit a radiation image acquired in the radiation imaging to a medical image management system.

11. A radiation imaging control apparatus comprising:
a reception unit configured to receive information corresponding to a radiation order for radiation imaging;
an instruction unit configured to issue an instruction for starting radiation imaging corresponding to the radiation order;
a determination unit configured to determine whether or not the radiation order has been already finished once, in a case where the instruction for the radiation order is issued; and
a control unit configured to limit a transmission of information indicating the radiation order is started, based on determination of the determination unit.

12. A radiation imaging system comprising:
an examination order acquisition unit configured to acquire an examination order via a network;
an imaging unit configured to capture an image of a patient using a radiation according to a content of the examination order;
a progress management server configured to manage progress of the examination order;
a first information notification unit configured to notify the progress management server of first information of starting and ending the examination for the examination order;
a re-examination unit configured to resume the ended examination whose first information has been already notified; and
a second information notification unit configured to notify the progress management server of second information of starting and ending the examination for the examination order corresponding to the resumed examination.

13. The radiation imaging system according to claim 12, further comprising:
a resumption examination information storage unit configured to store examination information corresponding to the resumed examination.

14. The radiation imaging system according to claim 13, further comprising:
a purpose selection unit configured to select one of re-imaging or additional imaging as a resumption purpose for the resumed examination,
wherein the second information notification unit is configured to notify the progress management server of the second information in a case where the additional imaging is performed for the resumption purpose, and is configured to not notify the progress management server in a case where the re-imaging is performed for the resumption purpose, and
wherein the resumption examination information storage unit stores resumption examination information.

15. The radiation imaging system according to claim 14, further comprising:
an accounting control server configured to control accounting information for the examination order; and
a resumption examination information transfer unit configured to transfer the stored resumption examination information to the accounting control server.

16. The radiation imaging system according to claim 14, further comprising:
an image transfer unit configured to transfer the captured image to an image management server,
wherein the resumption examination information is provided as supplementary information of the captured image in the examination resumed by the re-examination unit.

17. The radiation imaging system according to claim 14, wherein, if re-imaging is selected as a resumption purpose, the purpose selection unit is configured to treats the examination image captured before the resumption as an imaging error.

18. A method of controlling radiation imaging, the method comprising:
receiving information corresponding to a radiation order for radiation imaging;
transmitting information indicating a first state of a radiation order, in which corresponding radiation imaging is started but not finished, and to transmit information indicating a second state of the radiation order, in which corresponding radiation imaging is finished; and
limiting a transmission of information indicating the first state of the radiation order, in a case where an instruction is issued for re-starting radiation imaging corresponding to the radiation order after the information indicating the second state of the radiation order has been transmitted.

19. A non-transitory computer-readable storage medium storing a program read and executed by a computer to perform the method of claim 18.

20. A method of controlling radiation imaging, the method comprising:

receiving information corresponding to a radiation order for radiation imaging;

issuing an instruction for starting radiation imaging corresponding to the radiation order;

determining whether or not the radiation order has been already finished once, in a case where the instruction for the radiation order is issued; and limiting a transmission of information indicating the radiation order is started, based on a determination in the determining.

21. A non-transitory computer-readable storage medium storing a program read and executed by a computer to perform the method of claim 20.

22. An information processing method of a radiation imaging system including a progress management server for managing progress of an examination order, the method comprising:

acquiring an examination order via a network;

capturing an image of a patient using a radiation according to a content of the examination order;

notifying the progress management server of first information of starting and ending the examination for the examination order;

resuming the ended examination whose first information has been already notified; and notifying the progress management server of second information of starting and ending the examination for the examination order corresponding to the resumed examination.

23. A non-transitory computer-readable storage medium storing a program read and executed by a computer to perform the method of claim 22.

* * * * *